(12) United States Patent
Kase et al.

(10) Patent No.: US 6,333,293 B1
(45) Date of Patent: Dec. 25, 2001

(54) PROCESS FOR PREPARING A CATALYST FOR USE IN PRODUCTION OF METHACRYLIC ACID AND PROCESS OF PREPARING METHACRYLIC ACID

(75) Inventors: Yuichi Kase, Himeji; Naomasa Kimura, Okayama; Hideo Onodera, Himeji, all of (JP)

(73) Assignee: Nippon Shokubai Co., Ltd., Osaka-fu (JP)

( * ) Notice: Subject to any disclaimer, the term of this patent is extended or adjusted under 35 U.S.C. 154(b) by 0 days.

(21) Appl. No.: 09/593,701

(22) Filed: Jun. 15, 2000

(30) Foreign Application Priority Data

Jun. 15, 1999 (JP) ............................................. 11-167612

(51) Int. Cl.$^7$ ............................ B01J 27/18; B01J 27/19; B01J 27/198; B01J 27/199
(52) U.S. Cl. ........................ 502/211; 502/208; 502/209; 502/210
(58) Field of Search ............................... 502/208, 209, 502/210, 211

(56) References Cited

U.S. PATENT DOCUMENTS

| 3,965,163 A | | 6/1976 | Oda et al. | |
|---|---|---|---|---|
| 4,335,018 A | * | 6/1982 | Franz et al. | 502/209 |
| 4,487,962 A | * | 12/1984 | Krabetz et al. | 562/534 |
| 4,564,607 A | * | 1/1986 | Yoneda et al. | 502/209 |
| 4,925,823 A | | 5/1990 | Krabetz et al. | |
| 5,168,090 A | * | 12/1992 | Ebner et al. | 502/209 |
| 5,422,326 A | | 6/1995 | Kuroda et al. | |

FOREIGN PATENT DOCUMENTS

| EP | 0467144 | 1/1992 |
|---|---|---|
| EP | 0510566 | 10/1992 |
| EP | 0543019 | 5/1993 |
| EP | 0639404 | 2/1995 |
| GB | 1498595 | 1/1978 |
| GB | 2037604 | 7/1980 |
| JP | 50-37710 | 4/1975 |
| JP | 63-315148 | 12/1988 |
| JP | 8-10621 | 1/1996 |
| JP | 10-258233 | 9/1998 |

* cited by examiner

Primary Examiner—Elizabeth D. Wood
(74) Attorney, Agent, or Firm—Wenderoth, Lind & Ponack, L.L.P.

(57) ABSTRACT

The present invention provides a process for preparing a catalyst and the same for use in production of methacrylic acid, which is characterized by molding a raw material including a powder containing phosphorus and molybdenum at the specific pressure. The invention also provides a process for preparing methacrylic acid by gas phase oxidation and/or oxidative dehydrogenation of at least one compound selected from the group consisting of methacrolein, isobutyraldehyde and isobutyric acid in the presence of the catalyst

7 Claims, No Drawings

PROCESS FOR PREPARING A CATALYST FOR USE IN PRODUCTION OF METHACRYLIC ACID AND PROCESS OF PREPARING METHACRYLIC ACID

BACKGROUND OF THE INVENTION

1. Field of the Invention

This invention relates to a process of preparing a catalyst for use in production of methacrylic acid and the catalyst and also relates to a process of preparing methacrylic acid in the presence of the catalyst, more particularly, to the process of preparing the catalyst and the same which is suitable for preparing methacrylic acid by gas phase oxidation and/or oxidative dehydrogenation of at least one compound selected from the group consisting of methacrolein, isobutyraldehyde and isobutyric acid and the process for preparing methacrylic acid in the presence of the catalyst.

2. Description of the Prior Art

There have been many proposals concerning a catalyst for preparing methacrylic acid by gas phase oxidation of methacrolein, isobutyraldehyde and unsaturated aldehyde and a process thereof. For example, in the case of using methacrolein, there have been also many proposals about improving a catalyst such as heteropoly-acids. These proposals were divided into two categories. One is concerning a composition of a catalyst and the choice of the composition and another is concerning a regulation of catalyst properties and a process thereof with good reproducibility. According to the later, for example, it is described that the preferred specific surface area of a catalyst ranges from 0.01 to 5 $m^2/g$ and 0.01 to 50 $m^2/g$ in Japan Open-Laid No.49-116022 and Japan Open-Laid No.50-37710, respectively. In spite of these specification, this catalyst is not suitable for industrial use because of excessively high reaction temperature and low selectivity.

Many proposals concerning the control of pore structure of a catalyst have been done. For example, Japan Open-Laid No.51-136615 and Japan Open-Laid No.55-73347 propose a catalyst which is achieved by adding organic substances such as multivalent alcohol and polyvinyl alcohol and then curing them. However, the organic substances, which is used as additive and has a high decomposition temperature, will burn by heat treatment and thereby cause sintering and reduction of a catalyst and a problem such as low reproducibility of a catalyst still remains. Japan Open-Laid No.4-367737 proposed a process, wherein an organic polymer such as polymethylmethacrylate and polystyrene, which decomposes into a monomer and vaporizes at a relatively low temperature, is added, this method is also insufficient in the reproducibility of a catalyst.

In addition, a molding process, where a dried powder containing catalytic composition with the particle size adjusted in the range of 1 to 250 $\mu$m is used as a raw material, was proposed for the preparation of a catalyst in Japan Open-Laid 8-10621. However this process is not insufficient for industrial use, since this process has a problem of low reproducibility and also needs a more complicated drying process.

A catalyst for industrial use is generally used as a molded article. A molded article is produced by the process such as press molding, extrusion molding, rolling molding, Marumerizer molding, fluidized granulation, centrifuge fluidized coating process and the like. However, it is very hard to mold without lowering performance of a catalyst, and performance of the obtained catalyst is usually insufficient in reproducibility. For example, examples using press molding process were disclosed in Japan Open-Laid No.63-315148, Japan Open-Laid No.8-10621, Japan Open-Laid No.10-258233 and Japan Patent Gazette No.3-58776. According to all examples of them, a process of a press molding was not investigated in detail and these disclosures were insufficient from the view point of the reproducibility.

SUMMARY OF THE INVENTION

An object of the invention is to provide a process of preparing a catalyst for use in production of methacrylic acid and the catalyst. Another object of the invention is to provide a process for preparing methacrylic acid in the presence of the catalyst. The present inventors found that the above mentioned object can be achieved by molding a raw material including a powder containing phosphorus and molybdenum at the specific range of pressure and have accomplished the invention.

In other words, this invention provides a process for preparing a catalyst and the same for use in production of methacrylic acid by gas phase oxidation and/or oxidative dehydrogenation of at least one compound selected from the group consisting of methacrolein, isobutyraldehyde and isobutyric acid. The process comprises:

molding a raw material including a powder containing phosphorus and molybdenum at the pressure of 50 $kgf/cm^2$ to 5000 $kgf/cm^2$ into an article; and calcining the molded article to obtain a catalyst The invention also provides a process for preparing methacrylic acid characterized by gas phase oxidation and I or oxidative dehydrogenation of at least one compound selected from the group consisting of methacrolein, isobutyraldehyde anti isobutyric acid with molecular oxygen or a gas containing molecular oxygen in the presence of the catalyst produced by a method of the invention.

DESCRIPTION OF THE PREFERRED EMBODIMENT

The process for preparing the catalyst of the invention is characterized by molding a raw material including a powder containing phosphorus and molybdenum as an essential component at the pressure of 50 to 5000 $kgf/cm^2$ into an article and calcining the molded article to obtain a catalyst.

First, the raw material used for the invention will be described. The raw material includes a powder containing phosphorus and molybdenum( hereinafter referred as P/Mo containing powder).

The P/Mo containing powder may contain other elements, for example vanadium, copper, zinc, silver, arsenic, antimony, zirconium, cerium, alkali metal, alkaline earth metal and the like besides phosphorus and molybdenum.

Preferably, a weight of the P/Mo containing powder is reducible from 0 to 40%, preferably 2 to 35%, more preferably 4 to 30% by weight with respect to the weight of the P/Mo containing powder while the P/Mo containing powder is heated at 300° C. in the atmosphere or an inert gas. The weight of the P/Mo containing powder will be substantially constant after an elapse of 2hours of heat treatment. The weight loss of the P/Mo containing powder can be determined at that time if a weight of the P/Mo containing powder will be substantially constant after an elapse of 30 mins. or an hour. When a weight of the P/Mo containing powder is reduced over 40% by weight with respect to the weight of the powder, the fluidity of the powder deteriorate because the powder becomes sticky.

Preferably the P/Mo containing powder substantially comprises of particles having a diameter of 150 to 1500 $\mu$m, preferably 250 to 1000 μm, more preferably 250 to 800 μm. In the case of particle size below 150 μm, the fluidity of the P/Mo containing powder and runnability of molding conducted by the following molding process deteriorate and the selectivity for COx of the resultant catalyst is liable to increase because a pore size of the molded article becomes smaller. On the other hand, in the case of particle size over 1500 μm of the P/Mo containing powder, the amount of the P/Mo containing powder sucked into the mortar of a molding apparatus is variable and it causes to vary the molding pressure. As a result, mechanical properties of the resultant molded article and performance of the catalyst therefrom are liable to be lower because a pore size of the molded article becomes larger.

The P/Mo containing powder is prepared by a conventional method for a catalyst known to those of ordinary skill in the art. For example, compounds which contain phosphorus and molybdenum respectively are dissolved and dispersed into the medium usually into water to obtain a solution or slurry(hereinafter referred to as suspension).

The suspension is condensed, dried and calcined where necessary to prepare a powder. The suspension can be prepared by a conventional method such as evaporating concentration process, oxide mixing process and coprecipitation process and the like known to those skilled in the art, as long as the composition of the suspension is not remarkably uneven. Specifically, the suspension containing phosphorus and molybdenum can be prepared from the compounds such as oxide, nitrate, carbonate, hydride, chloride and ammonium salt of each element. For example, the following compounds can be used for the preparation of the suspension. Examples of compounds having molybdenum include molybdenum trioxide, molybdic acid and ammonium paramolybdate and the like. Examples of compounds having phosphorus include orthophosphoric acid, phosphorus pentoxide and ammonium phosphate and the like. Examples of compounds having vanadium include vanadium pentoxide, ammonium metavanadate and the like. Examples of compounds having copper, zinc, silver, arsenic, antimony, zirconium and cerium and the like include oxide, nitrate, carbonate, hydride, chloride, ammonium salt of each element. Examples of compounds having alkali metal and alkaline earth metal include nitrate, carbonate, hydride, chloride. Molybdophosphoric acid, molybdovanadophosphoric acid and ammonium salt of these acids and alkali metal salt also can be used.

The suspension can be dried by a well known methods such as evaporation drying, spray drying, drum drying, flash drying, drying under a reduced pressure, freeze drying and the like. Spray drying, drum drying and flash drying are preferable among them because these methods can simplify a process of pulverizing and screening particles with the desired diameter, preferably between150 to 1500 μm.

In addition to the P/Mo containing powder described above, the raw material used for the invention further comprises a lubricant and/or a reinforcement. Examples of the lubricant include graphite, talc, starch, palmitic acid, stearic acid and stearate. Examples of the reinforcement include inorganic fiber such as glass fiber and any type of whisker which are known for improving the mechanical properties of a catalyst and an attrition resistance. A lubricant and/or a reinforcement can be mixed with the P/Mo containing powder to obtain the raw material.

The raw material of the invention is molded at the pressure of 50 to 5000 kgf/cm$^2$, preferably 200 to 3500 kgf/cm$^2$, more preferably 600 to 2500 kgf/cm$^2$ into an molded article In the case of molding below the pressure of 50 kgf/cm$^2$, mechanical properties of the resultant molded article falls and performance of the catalyst therefrom is getting lower because a pore size of the catalyst becomes large. In the case of molding over the pressure of 5000 kgf/cm$^2$, the selectivity for COx of the resultant catalyst is liable to increase because a pore size thereof becomes too small. An excellent performance and a good reproducibility of the catalyst can be achieved by molding at the range of the pressure of 50 to 5000 kgf/cm$^2$.

The raw material can be molded into a molded article by any molding apparatus. The molded article has no limitation on its shape. Examples of the shape of the molded article include pellet, sphere, ring and tablet. The preferred shape of the molded article is a ring, because the shape of a ring expands surface area of a catalyst and thereby enables oxidation more effectively. The molded article also has no limitation on its size and usually has the size of 1 to 20 mm, preferably 3 to 5mm in the average diameter.

The molded article is calcined to obtain a catalyst at a temperature preferably between 300° C. to 600° C., more preferably 350° C. to 500° C. The preparation of the catalyst may be carried out in the presence of a nitrogen containing heterocyclic compound such as pyridine and quinoline. In this case, N containing heterocyclic compound may be removed by heat treatment after molding.

According to the process of preparing the catalyst of the invention, the catalyst with excellent performance can be produced with good reproducibility. The catalyst prepared by the process of the invention has no limitation on its composition, as long as the catalyst contain phosphorus and molybdenum and can be used for preparing methacrylic acid by oxidation and/or oxidative dehydrogenation of at least one compound selected from the group consisting of methacrolein, isobutyraldehyde and isobutyric acid. The preferable composition of the catalyst may be shown by the following equation(1).

$$P_a Mo_b V_c A_d B_e C_f O_x \qquad (1)$$

wherein P is phosphorus, Mo is molybdenum, V is vanadium, A is at least one element selected from the group consisting of copper, zinc and silver, B is at least one element selected from the group consisting of arsenic, antimony, zirconium and cerium, C is at least one element selected from the group consisting of alkali metal and alkaline earth metal, O is oxygen and a, b, c, d, e, f and x denote the ratio of atom of P, Mo, V, A, B, C and O, respectively and a=0.5 to 4, b=12, 0<c≦4,0<d≦3,0≦e≦5, f=0.01 to 4 and x is the number determined by the valance states of the other elements.

According to the invention, the process for preparing metbacrylic acid by gas phase oxidation and/or oxidative dehydrogenation of at least one compound selected from the group consisting of methacrolein, isobutyraldehyde and isobutyric acid with molecular oxygen or a gas containing molecular oxygen is characterized by the oxidation and oxidative dehydrogenation being carried out in the presence of the catalyst which is produced by the process of the invention.

In the invention, the term "preparing methacrylic acid by oxidation and/or oxidative dehydrogenation of at least one compound selected from the group consisting of methacrolein, isobutyraldehyde and isobutyric acid" denotes the general term of preparing methacrylic acid by oxidation of methacrolein, preparing methacrylic acid by oxidation and oxidative dehydrogenation of isobutyraldehyde, preparing methacrylic acid by oxidative dehydrogenation of isobutyric acid and the combination of these processes.

The gas phase oxidation and oxidative dehydrogenation for preparing methacrylic acid of the invention is not restricted in terms of the condition and an apparatus except for using the catalyst of the invention and can be carried out by a conventional method known to the skilled in the art.

A raw material supplied to oxidation and oxidative dehydrogenation(hereinafter referred as a raw material for methacrylic acid) is preferably a mixed gas including at least one compound selected from the group consisting of methacrolein, isobutyraldehyde and isobutyric acid, molecular oxygen and an inert gas as diluent. The mixed gas preferably contains 1 to 10 volume % of at least one compound selected from the group consisting of methacrolein, isobutyraldehyde and isobutyric acid. The mixed gas contains molecular oxygen and the volume of molecular oxygen is usually 1 to 10 times as much as that of at least one compound selected from the group consisting of methacrolein, isobutyraldehyde and isobutyric acid. The mixed gas also contains an inert gas as diluent and examples of an inert gas include nitrogen, carbon dioxide and steam and the like. Especially, steam is preferable because steam inhibits generation of by-product and is suitable for improving yield of methacrylic acid. Gas phase oxidation is carried out by reacting the mixed gas at 200 to 400° C. under normal pressure to 10 atm. at the space velocity of 100 to 5000 $hr^{-1}$(STP) in the presence of the catalyst of the invention. When methacrolein is used as a raw material for methacrylic acid, methacrolein is not necessarily pure. A gas containing methacrolein which is obtained by contact catalytic reaction of isobutylene, t-butanol and methyl-t-butylether can be used. Especially this gas can be preferably used for the industrial process of preparing methacrylic acid.

According to the process for preparing methacrylic acid of the invention, methacrylic acid can be produced in high yield by gas phase oxidation and/or oxidative dehydrogenation of at least one compound selected from the group consisting of methacrolein, isobutyraldehyde and isobutyric acid.

EXAMPLE

The following examples illustrate the invention; however these examples are intended to illustrate the invention and are not to be construed to limit the scope of the invention.

Conversion, selectivity and single pass yield are defined as follows:

% conversion=100×( moles of reacted raw materials)/( moles of raw materials fed)

% selectivity=100×( moles of produced methacrylic acid)/(moles of reacted raw materials)

% single pass yield=100×( moles of produced methacrylic acid)/( moles of raw materials fed)

Example 1

(Preparation of a Catalyst)

1766 g of ammonium paramolybdate and 106 g of ammonium metavanadate were added to 8 liter( hereinafter abbreviated as L) of heated ion-exchange water and dissolved while agitating to obtain a solution. 105 g(85 wt % solution) of phosphoric acid was added into the solution. Then another solution of 162 g of cesium nitrate and 10 g of copper nitrate being dissolved into 2 L of ion-exchange water was added into the solution while agitating and heating the solution to prepare a suspension.

A portion of the suspension was condensed and heated to obtain a slurry. The slurry was heated and dried at 130° C. for 15 hours, and then pulverized and screened to obtain 16 to 60 mesh( 250 to 1000 $\mu$m) of a P/Mo containing powder. This powder was heated at 300° C. In atmosphere to determine the weight loss of the P/Mo containing powder. The weight of this powder was reduced by 20% weight with respect to the P/Mo containing powder. A graphite was added into the P/Mo containing powder to obtain a raw material so that the raw material contains a graphite by 3 weight %. The raw material was molded at the pressure of 1000 kgf/cm$^2$ into the molded article of a pellet having 5.0 mm in diameter and 5.0 mm in length by a rotary press VIRGO(Kikusui manufacturing). The molded article was calcined at 400° C. for 2 hours in the air subsequently to 400° C. for 2 hours in a nitrogen gas to obtain a catalyst (1).

The composition of the catalyst (1) is shown as follows by the ratio of atom( the ratio of atom except for oxygen, the same applies hereinafter).

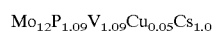

$$Mo_{12}P_{1.09}V_{1.09}Cu_{0.05}Cs_{1.0}$$

(Oxidation)

1500 ml of the catalyst (1) was charged into a steel reactor with the size of 25.4 mm in diameter. To the steel reactor, a mixed gas was supplied, which contains 3.5 volume % of methacrolein, 9 volume % of oxygen and 20 volume % of steam and was prepared by gas phase catalytic oxidation of isobutylene in the presence of a multi-element catalyst such as molybdenum-cobalt-tungsten-iron oxide at 340° C. The oxidation of the mixed gas was carried out at 280° C. and at space velocity of 1200 hr$^{-1}$ (STP). This result is shown in table 1.

Example 2

A catalyst (2) was prepared in the same manner of Example 1 except that the raw material was molded at the pressure of 3000 kgf/cm$^2$ for the preparation of a catalyst. The oxidation was carried out in the presence of the catalyst (2) in the same manner of Example 1. This result is shown in table 1.

Comparative Example 1

A catalyst (3) was prepared in the same manner of Example 1 except that the raw material was molded at the pressure of 40 kgf/cm$^2$ for the preparation of a catalyst. The oxidation was carried out in the presence of the catalyst (4) in the same manner of Example 1. This result is shown in table 1.

Comparative Example 3

A catalyst (5) was prepared in the same manner of Example 1 except that the raw material was molded by the extrusion molding process instead of molding at the pressure of 1000 kgf/cm$^2$ for the preparation of a catalyst. The oxidation was carried out in the presence of the catalyst (5) in the same manner of Example 1. This result is shown in table 1.

Example 3

A catalyst (6) was prepared in the same manner of Example 1 except that a slurry was dried at 250° C. for 15 hours after the slurry was heated and condensed to obtain a P/Mo containing powder. The P/Mo containing powder was heated at 300° C. In the atmosphere to determine the weight loss of the powder. The weight of the powder was reduced by 7 weight % with respect to the powder. The oxidation was carried out in the presence of the catalyst (6) in the same manner of Example 1. This result is shown in table 1.

Example 4

A catalyst (7) was prepared in the same manner of Example 1 except that the raw material includes stearic acid powder as a lubricant for the preparation of a catalyst. The oxidation was carried out in the presence of the catalyst (7). The result is shown in table 1.

Example 5

A catalyst (8) was prepared in the same manner of Example 1 except that the molded article has the shape of a ring having 5 mm in outside diameter and 2mm in internal diameter and 5 mm in length for the preparation of a catalyst. The oxidation was carried out in the presence of the catalyst (8). This result is shown in table 1.

| No. | preparing a catalyst | of IBAL (mole %) | MAL (mole %) | MAA (mole %) | MAA (mole %) |
|---|---|---|---|---|---|
| Ex. 6 | Press 1000 kgf/cm$^2$ | 100 | 10.1 | 68.2 | 68.2 |
| Com. Ex. 4 | Extrusion molding | 100 | 12.2 | 63.5 | 63.5 |

IBAL: Isobutyraldehyde, MAL: Methacrolein, MAA: Methacrylic acid
Raw material gas: gas including isobutyraldehyde
Reaction temperature: 280° C.

As shown in table 2, the catalyst of the invention was effective in the case of using isobutyraldehyde as a raw material gas and single pass yield of methacrylic acid prepared in the presence of the catalyst of the invention was higher than that of a catalyst prepared by extrusion molding.

Example 7

The oxidation was carried out in the same manner of Example 1 except that a mixed gas consisting of 4.5 volume

TABLE 1

| No. | Drying condition of slurry | Weight Loss (300° C.) (wt %) | Molding Method | Pressure (kgf/cm$^2$) | Shape of catalyst | Conversion of MAL (mole %) | Selectivity of MAA (mole %) | Single Pass Yield of MAA (mole %) |
|---|---|---|---|---|---|---|---|---|
| Ex. 1 | 130° C., 15 hrs | 20 | Press | 1000 | pellet | 84.1 | 83.6 | 70.3 |
| Ex. 2 | 130° C., 15 hrs | 20 | Press | 3000 | pellet | 86.5 | 81.1 | 70.2 |
| Com.Ex.1 | 130° C., 15 hrs | 20 | Press | 6000 | pellet | 87.1 | 76.1 | 66.3 |
| Com.Ex.2 | 130° C., 15 hrs | 20 | Press | 40 | pellet | 73.6 | 83.9 | 61.8 |
| Com.Ex.3 | 130° C., 15 hrs | 20 | Extrusion | — | pellet | 80.5 | 80.3 | 64.6 |
| Ex.3 | 250° C., 15 hrs | 7 | Press | 1000 | pellet | 85.2 | 82.5 | 70.3 |
| Ex.4 | 130° C., 15 hrs | 20 | Press | 1000 | pellet | 84.5 | 83.6 | 70.6 |
| Ex.5 | 130° C., 15 hrs | 20 | Press | 1000 | ring | 84.2 | 85.5 | 72.0 |

MAL: methacrolein, MAA: methacrylic acid
Raw material gas: mixed gas including methacrolein
Temperature of oxidation of methacrolein: 280° C.

As shown in table 1, the conversion of methacrolein in the case of molding at the pressure of 1000 to 3000 kgf/cm$^2$ was from 84.1% to 85.2% and stable oxidation of methacrolein was carried out. It has been apparent that single pass yield of methacrylic acid in the case of molding at the range of the pressure of 1000 to 3000 kgf/cm$^2$ was higher than that in the case of molding at the pressure of 40 kgf/cm$^2$ and 6000 kgf/cm$^2$, respectively. Single pass yield of methacrylic acid was highest, especially in the case of using the catalyst with the shape of a ring.

Example 6

The oxidation was carried out in the same manner of Example 1 except that a mixed gas consisting of 4.0 volume % of isobutyraldehyde, 10 volume % of oxygen, 12 volume % of steam and 74 volume % of nitrogen is used as a raw material gas and space velocity was changed into 1000 hr$^{-1}$. This result is shown in table 2.

Comparative Example 4

The oxidation was carried out in the same manner of Example 6 except that the catalyst (1) was replaced by the catalyst (5). The result is shown in table 2.

TABLE 2

| | Condition of | Conversion | Selectivity of | Selectivity of | Single Pass Yield of |

% of isobutyric acid, 12 volume % of oxygen, 12 volume % of steam and 71.5 volume % of nitrogen was used as a raw material gas and space velocity was changed into 1500 hr$^{-1}$. This result is shown in table 3.

Comparative Example 5

The oxidation was carried out in the same manner of Example 7 except that the catalyst (1) was replaced by the catalyst (5). The result is shown in table 3.

TABLE 3

| No. | Condition of preparing a catalyst | Conversion of IBA (mole %) | Selectivity of MAA (mole %) | Single Pass Yield of MAA (mole %) |
|---|---|---|---|---|
| Ex.7 | Press 1000 kgf/cm$^2$ | 99.5 | 79.6 | 79.2 |
| Com. Ex. 5 | Extrusion molding | 97.1 | 77.5 | 75.3 |

IBA: Isobutyric acid, MAA: Methacrylic acid
Raw material gas: gas including isobutyric acid
Reaction temperature: 280° C.

As shown in table 3, the catalyst of the invention was effective in the case of using isobutyric acid as a raw material gas and single pass yield of methacrylic acid prepared in the presence of the catalyst of the invention was higher than that of a catalyst prepared by extrusion molding.

This application is based on patent application No.11-167612 filed in Japan, the contents of which is hereby incorporated by reference. Other embodiments and variations will be obvious to those skilled in the art, and this invention is not to be limited to the specific matters stated above.

What is claimed is:

1. A process for preparing a catalyst for use in production of methacrylic acid by gas phase oxidation and/or oxidative dehydrogenation of at least one compound selected from the group consisting of methacrolein, isobutyraldehyde and isobutyric acid, which comprises:

molding a raw material including a powder containing phosphorus and molybdenum at the pressure of 50 kgf/cm$^2$ to 5000 kgf/cm$^2$ into an article; and calcining the molded article to obtain a catalyst.

2. The process of claim 1, wherein a weight of the powder is reducible from 0 to 40% by weight with respect to the weight of the powder by heating at a temperature of 300° C.

3. The process of claim 1, wherein the powder comprises particles having a diameter of 150 μm to 1500 μm.

4. The process of claim 1, wherein the raw material further comprises a lubricant and/or a reinforcement.

5. The process of claim 1, wherein the molded article has a shape of a ring.

6. The process of claim 1, wherein the powder is obtained by drying a material containing phosphorus and molybdenum by at least one method selected from the group consisting of spray drying, drum drying and flash drying.

7. A catalyst produced by the process of claim 1, which comprises the following composition of the formula (1):

$$P_a Mo_b V_c A_d B_e C_f O_x \qquad (1)$$

wherein P is phosphorus, Mo is molybdenum, V is vanadium, A is at least one element selected from the group consisting of copper, zinc and silver, B is at least one element selected from the group consisting of arsenic, antimony, zirconium and cerium, C is at least one element selected from the group consisting of alkali metal and alkaline earth metal, O is oxygen and a, b, c, d, e, f and x denote the ratio of atom of P, Mo, V, A, B, C and O, respectively and a=0.5 to 4, b=12, 0<c≦4, 0<d≦3, 0≦e≦5, f=0.01 to 4 and x is the number determined by the valance states of the other elements.

* * * * *